(12) United States Patent
Ergeneman et al.

(10) Patent No.: US 8,560,033 B2
(45) Date of Patent: Oct. 15, 2013

(54) MAGNETICALLY CONTROLLED WIRELESS OPTICAL OXYGEN SENSOR FOR INTRAOCULAR MEASUREMENTS

(75) Inventors: Olgac Ergeneman, Zurich (CH); Karl Vollmers, Saint Paul, MN (US); Jake J. Abbott, Salt Lake City, UT (US); Bradley Nelson, Zumikon (CH)

(73) Assignee: ETH Zurich, Zurich (CH)

( * ) Notice: Subject to any disclaimer, the term of this patent is extended or adjusted under 35 U.S.C. 154(b) by 1175 days.

(21) Appl. No.: 12/467,661

(22) Filed: May 18, 2009

(65) Prior Publication Data

US 2010/0022857 A1    Jan. 28, 2010

Related U.S. Application Data

(60) Provisional application No. 61/053,717, filed on May 16, 2008.

(51) Int. Cl.
*A61B 5/00*    (2006.01)

(52) U.S. Cl.
USPC ............................................ 600/318

(58) Field of Classification Search
USPC ............ 600/310, 318; 435/287.1; 174/122 G; 29/825, 868
See application file for complete search history.

(56) References Cited

U.S. PATENT DOCUMENTS

2006/0266543 A1*  11/2006  Clare et al. ................ 174/122 G

OTHER PUBLICATIONS

Shonat et al.: "Oxygen Tension Imaging in the Mouse Retina"; Annals of Biomedical Engineering, vol. 31, pp. 1084-1096, 2003.
Mathieu et al.: "Method of Propulsion of a Ferromagnetic Core in the Cardiovascular System through Magenetic Gradients Generated by an MRI System" IEEE Transactions on Biomedical Engineering, vol. 53, No. 2, Feb. 2006; pp. 292-299.
Ergeneman et al.: "A Magnetically Controlled Wireless Optical Oxygen Sensor for Intraocular Measurements" IEEE Sensors Journal, vol. 8, No. 1, Jan. 2008; pp. 29-37.
Nelson et al.: "A Magnetically Controlled Wireless Intraocular Oxygen Sensor: Concept, Prototype, and In Vitro Experiments" Proceedings of the 29th Annual Internationaal Conference of the IEEE EMBS Cite Internationale, Lyon, France, Aug. 23-26, 2007; pp. 4189-4193.
Yesin et al.: "Modeling and control of Untethered Biomicrorobots in a Fluidic Enviornment Using Elecromagenetic Fields" The International Journal of Robotics Research 2006; pp. 527-533.
Stefansson et al.: "Intraocular Oxygen Tension Measured with a Fiber-optic Sensor in Normal and Diabetic Dogs" Am. J. Physiol. Heart Circ. Physiol., vol. 256, pp. 1127-1133, 1989.

\* cited by examiner

*Primary Examiner* — Brian Szmal
(74) *Attorney, Agent, or Firm* — Leydig, Voit & Mayer, Ltd.

(57) ABSTRACT

A sensor for intraocular measurements moveable within at least one of an vitreous humor of an eye, an aqueous humor of an eye and an intraocular replacement medium. The sensor includes a magnetic body susceptible to magnetic fields and at least one sensor film.

14 Claims, 5 Drawing Sheets

MAGNETICALLY CONTROLLED WIRELESS OPTICAL OXYGEN SENSOR FOR INTRAOCULAR MEASUREMENTS

CROSS REFERENCE TO PRIOR APPLICATIONS

This application claims the priority of U.S. Provisional Patent Application No. 61/053,717, filed May 16, 2008. The entire disclosure of that application is incorporated by reference herein.

BACKGROUND

The present invention relates to a sensor and an apparatus for intraocular measurements, and a method to carry out such measurements.

FIELD

The retina of the living eye needs sufficient supply of oxygen and other nutrients to perform its primary visual function. Retinal hypoxia is a pathological condition in which the retinal tissue lack adequate oxygen supply. Such inadequate oxygen supply is correlated with major eye diseases including diabetic retinopathy, glaucoma, retinopathy of prematurity, age-related macular degeneration, and retinal vein occlusions. Retinal hypoxia is also presumed to initiate angiogenesis, which is a major cause of blindness in developed countries.

Hypoxia is typically present at the end stages of retinal diseases. However, during the early stages, the relation between blood flow sufficiency, vessel patency, and tissue hypoxia are still unknown. The influence of oxygen on said diseases is thus not well understood, and in vivo oxygen measurements would be essential for better diagnosis and treatment.

Measuring the concentration of molecular oxygen both in aqueous humor and vitreous humor, and particularly in the preretinal area, and the oxygen supply to the cornea and lens of the eye are of great practical interest in ophthalmologic research and treatment. For example the knowledge of the preretinal oxygen concentration would allow the more precise planning of eye operations, such as, for example, vitrectomy operations and/or laser photocoagulation operations, and the corresponding necessary aftercare. To address these issues, a number of intraocular oxygen measurement devices have been developed, The first reliable devices used for measuring oxygen concentrations in eye tissue have been polarographic (Clark) electrode oxygen sensors, which are based on the reduction of oxygen on a noble metal electrode as described by E. Stefansson et al., Am. J. Physiol. Heart Circ. Physiol., vol. 256, pp. 1127-1133, 1989. The electrode is usually surrounded by a membrane that is permeable to molecular oxygen and allows it to reach the electrode, where it is electrolytically reduced during the measuring process. The oxygen concentration is proportional to the current resulting from the reduction of oxygen at the surface of this electrode. Despite being accurate, their relative size, slow response time, motion dependency, and high invasiveness make them rather unsuitable for intraocular measurements. Furthermore this type of sensor also consumes oxygen, which might be problematic for low-oxygen-concentration environments. Moreover the need for electrical wiring to the sensor is problematic.

E. Stefansson et al., Am. J. Physiol. Heart Circ. Physiol., vol. 256, pp. 1127-1133, 1989 also describes fiber optical sensors based on fluorescence quenching. In this system, fluorescent dyes are packaged into a probe and the oxygen concentration is measured by means of fluorescence quenching The fluorescence signal is read by this probe or by an additional second probe, that is also inserted in the eye cavity. Unlike polarographic electrode oxygen sensors, the fiber-optic probe oxygen sensors do not consume oxygen, but they also suffer from excessive invasiveness R. D. Shonat, A. C. Kight, Ann. Biomed. Engin., vol. 31, pp. 1084-1096, 2001 describes how oxygen concentrations in the retina are measured with spectroscopic means, by injecting phosphorescence dyes directly into the eye cavity. Such a method is not applicable for human patients.

There are non-invasive technologies that measure retinal oxygen concentration indirectly, including those based on magnetic resonance and spectral imaging. However, these methods cannot provide quantitative measurements of oxygen concentrations within the retinal tissue affected by disease. The present invention overcomes these drawbacks and provides an apparatus and method for taking intra-ocular measurements of the concentration of chemical analytes or chemical and/or physical parameters.

SUMMARY

An aspect of the present invention is to provide an improved sensor for the intraocular measurement of the concentration of chemical analytes or chemical and/or physical parameters such as temperature, pH and/or the amount of glucose, oxygen and carbon dioxide.

Another aspect of the present invention is to provide an advantageous method for the measuring of the intraocular concentration of chemical analytes or chemical and/or physical parameters.

In an embodiment, the present invention provides for a sensor for intraocular measurements moveable within at least one of an vitreous humor of an eye, an aqueous humor of an eye and an intraocular replacement medium. The sensor includes a magnetic body susceptible to magnetic fields and at least one sensor film. The sensor is wireless.

BRIEF DESCRIPTION OF THE DRAWINGS

The present invention is described in greater detail below on the basis of embodiments and of the drawings in which:

FIGS. 3(a)-3(f), shows different embodiments of magnetic sensors according to the present invention. FIG. 3(a) depicts a spherical sensor, 3(b) depicts an ellipsoid sensor, FIG. 3(c) depicts a cylinder shaped sensor, FIGS. 3(d), 3(e) and 3(f) each depict a sensor that is a microfabricated assembled device.

DETAILED DESCRIPTION

Figure 1:
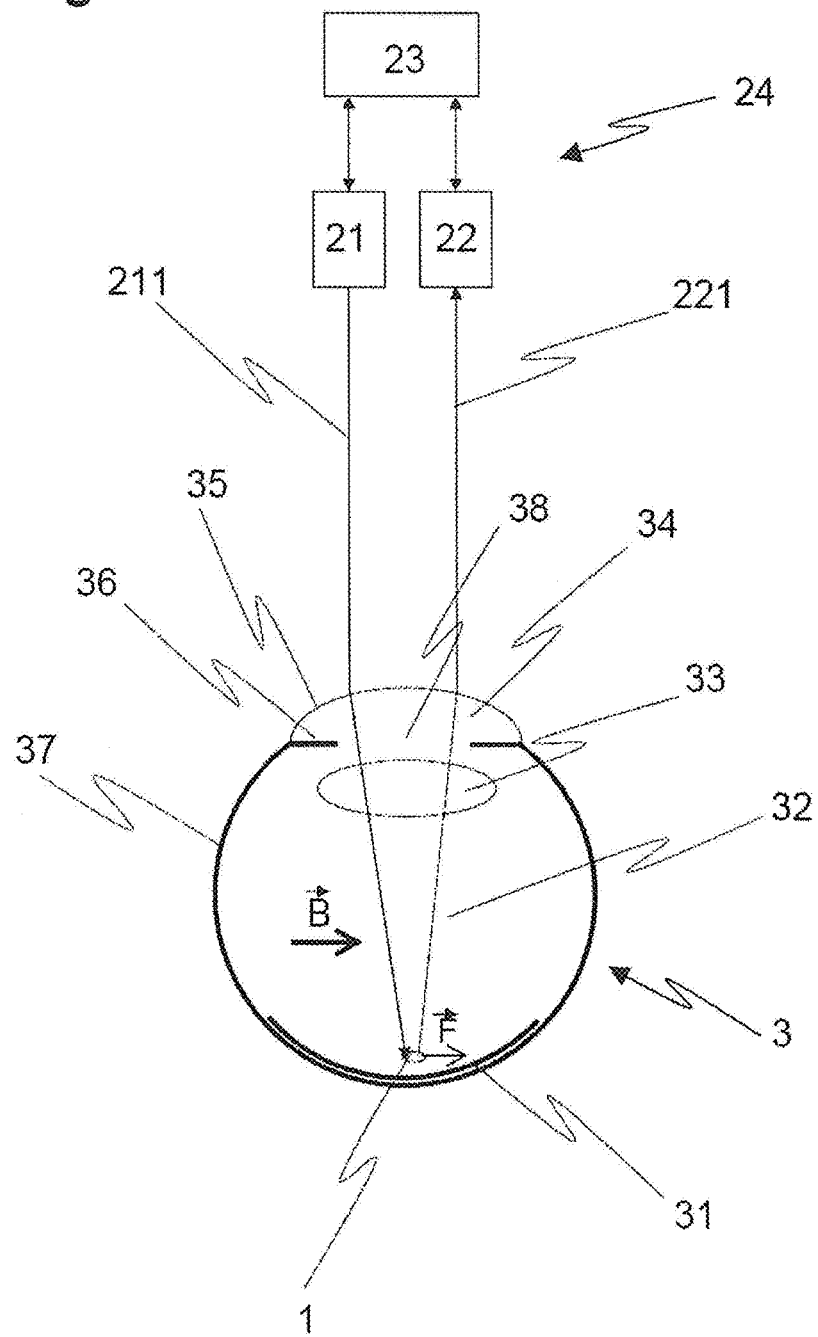
FIG. 1 schematically shows the apparatus according to the present invention, a patient's eye, and the sensor according to the present invention within the eye.

A wireless sensor for intraocular measurements according to the present invention comprises a magnetic body and a sensor film. The intraocular measurements that can be made with the intraocular sensors of the present invention include measurement of chemical analytes or chemical and/or physical parameters such as temperature, pH, the amount of glucose, oxygen and/or carbon dioxide present in the intraocular space. The sensor of the invention can also be used, for example, to measure the distribution of pharmaceutical ingredients in the eye. The magnetic body of the invention is susceptible to external magnetic fields and can be moved within the vitreous humor and the aqueous humor of a patient's eye by applying suitable magnetic fields. The sensor dye has a luminescence activity that depends on the concentration of an analyte, e.g. molecular oxygen, carbon dioxide and/or glucose, or an intrinsic physical or chemical parameter such as temperature or pH. For example, the luminescence intensity and lifetime can change in response to a change in the concentration of an analyte or a change in a physical or chemical parameter.

In order to be moveable by an applied magnetic field, the magnetic body of the sensor according to the present invention is susceptible to external magnetic fields. This can be achieved by using a magnetic body that is a permanent magnet, is made from a ferromagnetic, ferrimagnetic or paramagnetic material or contains a compound with magnetic properties inside the magnetic body (e.g., magnetic particles, nanoparticles and/or super paramagnetic nanoparticles dispersed in a polymer). When such a magnetic body is subject to a magnetic field gradient, a magnetic force acts on the magnetic body, which can then be used to move the sensor within the viscous fluid of the vitreous humor or aqueous humor of a patient's eye (or replacement medium). The magnetic body may have any suitable form a shape, e.g. the form of a sphere, a prolate or oblate spheroid, or a cylinder. In addition to such simply formed objects, it is also possible to employ more complicated shapes, produced for example with photolithographic techniques used for producing micro devices or any other fabrication technique to make microdevices such as molding, stereolithography, vacuum deposition, laser cutting and/or electroplating.

Depending on their particular geometry, the magnetic bodies of the invention can be subject to torques produced by the applied magnetic field, which may be used to orient the magnetic body in a three-dimensional space. The torque on the magnetic body can induce a rotational motion which in turn can be used to move the magnetic body, such as, for example, like a helical propeller.

An apparatus for intraocular measurements according to the present invention comprises a detection system and an actuation system. The detection system comprises a light source that is able to produce a directed light beam with a specific spectrum, for example, a single, narrow waveband, and a device for the detection of an impinging luminescence light signal. The apparatus includes a controller for the light source and the detection device, and a means for analyzing the detected luminescence light signal.

A method for intraocular measurements according to the present invention comprises the step of inserting the sensor according to the present invention into the vitreous humor or the aqueous humor of an eye, for example, through a small incision in the sclera, and in subjecting the eye to a controlled magnetic field and field gradient that causes the sensor to move within the vitreous humor or the aqueous humor of the eye. To obtain the desired measurement value, the sensor is moved to a predetermined position. An excitation light beam is directed to the sensor, exciting the luminescence sensing system. A luminescence light signal returning from the sensor is detected; and the detected signal is analyzed in order to obtain the measurement value at the position of the sensor. "Wireless" as used in the present application means that no wire connects the sensor with either the detection system or with the actuation system. The use of the sensor is not limited to the vitreous humor or the aqueous humor of an eye. It can also be used, for example, in in-vivo measurements in other areas of a human or animal body or in-vitro in, for example, a test tube or a petri dish. The sensor's use is not limited to biological uses.

Intraocular procedures are unique among in vivo procedures because they provide a direct line of sight through the pupil. This makes it possible to move a sensor according to the present invention very precisely in a patient's eye. In an embodiment of the present invention, the position of the sensor is continuously detected and tracked by optical means through the pupil. The detected position may be used for a closed-loop control of the movement of the sensor.

The sensor operates based on the quenching of luminescence in the presence of the analyte of interest, for example molecular oxygen. The sensor itself has no need for an internal energy supply. The energy for the translational movements of the sensor's magnetic body is a result of the applied external magnetic field, while the energy for the excitation of the luminescence dye that is used for the analyte measurements is delivered by the external excitation/light source. The detection of the luminescence signal necessary for the determination of the analyte concentration is realized optically. Both excitation and detection are carried out, for example, via the pupil of the eye. Thus no wiring is necessary. The applied external magnetic field also has no negative effect on the eye. The only invasive step of the measurement method according to the present invention is thus the insertion and subsequent removal of the sensor into the eye through the sclera. To further reduce the invasiveness, the sensor should be as small as possible, for example usually less than 4 mm long, such as less than 0.5 mm or even less than 0.25 mm in length. Since a reduction in size results in a lower signal-to-noise ratio, a compromise must be made between sensitivity and invasiveness.

The actuation system of an apparatus according to the present invention comprises means for producing a magnetic field including, for example, producing a magnetic field and/or magnetic field gradient through stationary or position-controlled electromagnets, position-controlled permanent magnets, a commercially-available MRI system and/or superconducting magnets. The actuating system also includes a controller for said means to move the sensor according to the present invention within the patient's eye. The device can be precisely controlled by applying magnetic forces or torques resulting from magnetic fields generated by coils or permanent magnets. Such actuating devices are well known to those skilled in the art.

Figure 7:
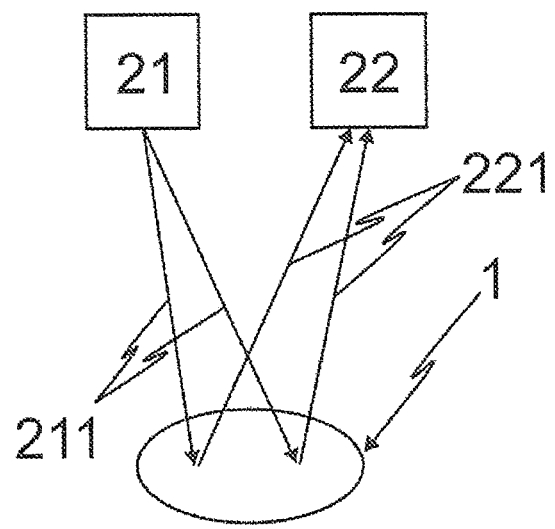
FIG. 7 shows a sensor which has been activated by a blue LED as an excitation source. The sensor's luminescence is also shown. Local concentration gradients can, for example, be obtained by reading out the different locations on the sensor.

In an embodiment of the present invention, local concentration gradients of the analyte of interest can be obtained by reading out different locations on the sensor. This can be achieved by using luminescence dyes with different emission and/or excitation spectra on different locations of the sensor body, or by using a readout system that can selectively read out different locations of the sensor body. The present invention includes sensors that allow the measurement of more than one parameter, one after another, or even at the same time It may be desirable to measure spatial gradients in a quantity. This can be accomplished by taking measurements while moving the sensor. However, these measurements will be separated in time, and the movement of the sensor could potentially affect the environment, particularly in a low Reynolds-number regime. It is possible to measure gradients directly with a stationary sensor. Specific locations on the sensor can, for example, be excited and sensed simultaneously, as depicted in FIG. 7. This requires the ability to focus the excitation signal on a specific region of the sensor. Clearly, this necessitates a greater level of sensing spatial resolution. Alternatively, multiple sensor films with different emission spectra can be excited simultaneously, and the emitted signals can be band-pass filtered.

A schematic embodiment of an apparatus according to the present invention is shown in FIG. 1. Shown is a sensor comprising an ellipsoid-shaped body 3.25 mm in length made of steel which has been inserted into an eye 3 of a patient through a small incision (not shown) in the sclera 37.

In a next step, a magnetic field generation device (not shown) which is part of the actuation system of the apparatus is activated, producing a controlled magnetic field B over the volume of the eye 1. The necessary magnetic fields, which may be on the order of milliTeslas to Teslas, may, for example, be generated by coils or permanent magnets. Magnetic field gradients, which may have magnitudes from 10 mT/m upto 50 T/m, can also be generated to apply forces on the magnetic body. The magnetic field generation device may also be custom-built. However, it is also possible to utilize a magnetic resonance imaging (MRI) apparatus for generating and controlling the necessary magnetic fields. For example, an MRI system which can be used for in-vivo procedures is a Siemens Avanto 1.5 T (Siemens Magnetom Avanto 1.5 T, Erlangen, Germany) with real-time feedback capabilities. Using the magnetic gradients coils, a magnetic force is induced in the ferromagnetic material of the sensor which allows the sensor to be moved in the considered environment. The propulsion force is proportional to the magnetic gradient amplitude, the sensor's volume and to the sensor's magnetization.

The generated magnetic field has a certain field gradient, resulting in a translational magnetic force F acting on the sensor 1. Depending on the geometry of the sensor, a torque may also be present. As a result, the sensor I moves through the vitreous humor 32 or the aqueous humor 34 of the eye, following a path predetermined by the field gradient. If a stable local equilibrium can be controlled using the magnetic field, the sensor will be stopped at the position of said local equilibrium. In that case, the magnetic field may be changed over time, in order to move the sensor, or it may remain constant. In the later case, the patient and/or the magnetic field generating device may be moved in three-dimensional space to move the sensor, since the movement of the sensor in the eye, while remaining in the local equilibrium, directly refers to the movement of the patient or the magnetic field generating device.

In an embodiment of the present invention, the sensor can be a sphere (or another shape) made of a hard magnetic material such as NdFeB, AlNiCo, SmCo and/or magnetic ferrites such as, for example, barium ferrite and/or strontium ferrite. "Hard magnetic material" in the present application is understood to include materials with coercivity of about 10 kAmps m$^{-1}$. The magnetization M of the material is essentially independent of the applied magnetic field H. In this embodiment, the magnetic force $F_{mag}$ on the sphere is calculated by the force on a magnetic dipole moment, $F_{mag}=\mu_0 v M$ VH, where v is the volume of the sphere and $\mu_0$ is the magnetic permeability of vacuum. There is also a magnetic torque on the dipole that tends to align the magnetization vector with the applied magnetic field vector H. For ferromagnetic and paramagnetic magnetic bodies, having a saturation magnetization value of $m_S$, the magnetization vector M will always align itself with the applied field H, since there is no shape anisotropy in a sphere. This leads to the simplification $F_{mag}=\mu_0 v$ |M|.V|H|. At relatively low fields, where |H|<$m_S$/3, the magnetization of a soft-magnetic sphere sensor is linearly related to the applied field, M=3H. If |H| is large enough to magnetically saturate the material, then is |M|=$m_S$. "Soft magnetic"in the present application is understood to include materials with coercivity of less than 10 kAmps m$^{-1}$, for example, 1 kAmps m$^{-1}$.

For magnetic bodies produced with MEMS techniques, the effective magnetization in dependence from an applied magnetic field can be determined experimentally. Reference is made, for example, to K. Berk Yesin et al., Int'l J. Robotics Research, vol. 25, pp. 527-536, 2006.

To avoid unnecessary damage to the eye tissues the position of the sensor should be continuously checked, particularly during a shift of its position. This may either be achieved by repeated X-Ray imaging or by direct optical observation through the pupil of the eye. This makes it possible to move the sensor very precisely. In an embodiment of the present invention, the position of the sensor is continuously detected and tracked, using, for example, a camera, the detected position being used for a closed-loop control of the movement and positioning of the sensor.

The function of the sensor is based on the quenching of luminescence in the presence of the analyte of interest, for example molecular oxygen. The sensor itself does not require an internal energy supply. The energy for the translational movements of the sensor's 1 magnetic body is a result of the applied external magnetic field, while the energy for the excitation of the sensor film that is used for the analyte measurements is delivered by an external light source 21. The detection of the luminescence light signal 221 used for the determination of the analyte concentration is carried out optically. Both the excitation light beam 211 and the signal light beam 221 returning from the sensor 1 are, for example, directed through the pupil 38 of the eye.

Photoluminescence is the emission of photons from a material, in response to absorption of some form of radiant energy. Well known examples are, for example, fluorescence and phosphorescence, where a dye molecule absorbs light at a certain wavelength, thereby being excited to a higher energy state. After internal relaxation processes, the molecule reaches a somewhat lower energy state, from which it spontaneously emits radiation at a wavelength longer than the excitation wavelength. The difference between excitation and emission wave lengths is called Stokes shift.

The intensity of the luminescent emission is the result of an equilibrium between excitation and the different radiant and non-radiant relaxation pathways and kinetics. Thus the intensity of the luminescent emission and its lifetime after excitation may be influenced by a variety of processes and parameters. For example, the luminescent emission is decreased very efficiently by molecular oxygen, by providing an efficient alternative non-radiant relaxation mechanism. This effect is known as quenching. Thus luminescence quenching is one method that is used to measure the oxygen concentration.

With suitable sensor films comprising a supporting matrix permeable to the analyte of interest and luminescence dyes such as, for example, metal-ligand complexes of rhenium (Re), ruthenium (Ru), osmium (Os), or iridium (Ir), other parameters may be determined via their direct or indirect influence on the luminescence signal. $[Ru(Ph_2phen)_3]^{2+}$ can, for example, be used as a fluorescence dye in the sensor film to measure a parameter such as oxygen. Almost any long-lived fluorophore can be used as a luminescence dye in the sensor film, particularly when dissolved in an organic solvent. Phosphorescence can be used in the sensor film to detect, for example, oxygen, due to its long decay time. Several porphyrin derivatives are highly oxygen-sensitive phophoresence dyes. These can also be used in the sensor film. One example is platinum(II) octaethylporphyrinketone (PtOEPK) from Joanneum Research, Graz, Austria, which has a large Stokes shift giving a lifetime of over 60 microseconds even when embedded in polystyrene. Certain dyes, such as carboxynaphthofluorescein (CNF) in poly (methylmethacrylate) or Pyr-PSDM-CNT pyrene-Poly(sulfadimethoxine methacrylamide)-carbon nanotubes, may have different excitation and emission spectra in a protonated and a deprotonated form, thus showing a luminescence behavior depending on the pH.

The quenching effect of oxygen can be described by the Stern-Volmer equations:

$$I_0/I = 1 + K[O_2] \qquad 1$$

and $$\tau_0/\tau = 1 + K[O_2], \qquad 2$$

where $I_0$ and $I$ are the luminescence intensities in the absence and in the presence of oxygen, respectively, and $\tau_0$ and $\tau$ are the luminescence lifetimes in the absence and presence of oxygen. K is the quenching constant, and $[O_2]$ is the oxygen concentration.

Luminescence quenching measurements for use in the present invention may be carried out in several ways:

The luminescence signal intensity from the sensor (1), changing in response to the oxygen quenching process, may, for example, be detected and analyzed. The analyte concentration can be calculated from the measured signal intensity. Although this method is straight-forward to implement, it suffers from limited accuracy and systematic errors. The intensity of light is extremely sensitive to extrinsic conditions, such as dye concentration, optical surface quality, fluctuations of the excitation source, photo-bleaching, incidence angle, absorption along the optical pathways, etc. These parameters, however, may change from sample to sample, from measurement to measurement, and are difficult to control and to properly take into account. The result may be considerable systematic measurement errors. While a sensor is moved in the ocular cavity, for example, the optical path distance from the light source 21 to the sensor 1 and back to the photo detector 22 is constantly changing, depending on the orientation and location of the sensor 1, thereby influencing the total light intensity detected by the sensor.

The problems of intensity-based measurements can be avoided by using a sensor using a wavelength-ratiometric sensor film, which has an absorption or emission spectrum that changes in the presence of an analyte. Some platinum complexes can be used as a luminescence dye in the sensor film for this purpose because they show two emission peaks. One emission intensity is sensitive to oxygen and the other emission is not sensitive to oxygen. The ratios of emission intensities at these two wavelengths can be measured to determine the oxygen concentration.

A highly sensitive ratiometric luminescence sensor film incorporating a supporting matrix doped with a luminophore such as metalloporphyrins as the luminescence dye and a reference dye in the sensor film can be used to detect analytes or physical or chemical parameters. One example of such a ratiometric luminescence oxygen sensor film incorporates a sol-gel supporting matrix doped with platinum or palladium tetrakis pentafluorophenyl porphine (PtTFPP or PdTFPP) as the sensitive material and 7-amino-4-trifluoromethyl coumarin (AFC) as the reference dye in the sensor film. Using an LED with a central wavelength of 400 nm as an excitation source, the emission wavelengths of the oxygen-sensitive dye and the reference dye, which have no spectral overlap, can be measured, and the oxygen concentration can be determined using a ratiometric-based method. The sensitivities of the PtTFPP-doped and PdTFPP-doped oxygen sensors are evaluated in terms of the ratio $I_{N2}/I_{O2}$, where $I_{N2}$ and $I_{O2}$ correspond to the detected luminescence intensities in pure nitrogen and pure oxygen, respectively.

Luminescence lifetimes can also be evaluated. Luminescence lifetime $\tau$ is an intrinsic property, unlike luminescence intensity. Extrinsic parameters conditions do not affect the lifetime of emission. Spontaneous photon emission is a random event, each excited dye molecule having the same probability of emitting a photon within a given period of time. This results in an exponential decay in the emission intensity, $I(t)=I(0)exp(-t/\tau)$, after a single excitation impulse. The lifetime of emission decreases in the presence of oxygen as a result of the quenching process. Hence, the oxygen concentration can be calculated from the lifetime of emission r, using the Stern-Volmer equation.

There are essentially two approaches that are used for measuring luminescence lifetimes: time-domain measurements and frequency-domain measurements. In time-domain measurements, a sample is excited with a light pulse, and the exponentially decaying luminescence intensity signal, changing as a function of time, is measured and analyzed to result lifetime $\tau$. In frequency-domain measurements, on the other hand, the sample is excited with a periodic signal that consequently causes a modulated luminescence emission at the identical frequency. Due to the lifetime of emission, the emission signal has a phase shift in respect to the excitation signal. The modulation signal used to modulate the excitation light source is used as a reference signal to establish a zero-phase position, and the lifetime $\tau$ is obtained by measuring the phase shift between the excitation signal and the emission signal. The relationship between the lifetime $\tau$ and the corresponding phase shift $\phi$ (in rad) for a simple exponential decay function is given by $\tau = \tan(\phi)/\omega$, where $\omega$ is the circular modulation frequency (in rad/s). Frequency-domain measurements are less demanding than time-domain measurements from a technical point of view, and also more accurate, since they can be carried out with continuous-wave irradiation. A further advantage is a better signal-to-noise ratio due to the reduction of 1/f noise by shifting the data acquisition frequency from DC for time-domain measurements to the modulation frequency. The influence of ambient light is also removed.

Figure 2:
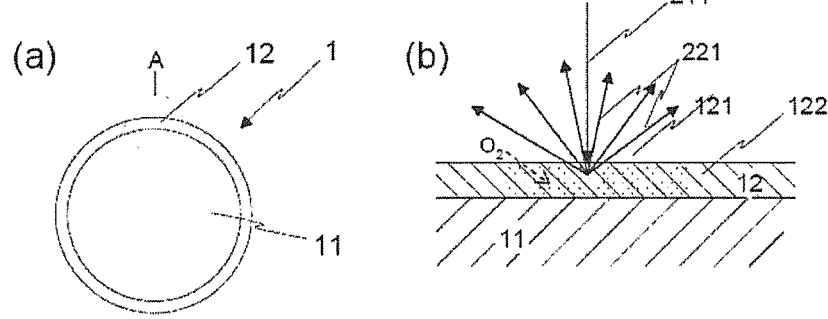
FIG. 2, including FIGS. 2(a) and 2(b), schematically shows a cross section of a sensor in an overall view FIG. 2(a), and a detailed view of the sensor film including the supporting matrix and the luminescence dye in FIG. 2(b).

An embodiment of the sensor 1 according to the present invention is schematically shown in FIG. 2, with a cross section of the sensor 1 in an overall view given in FIG. 2(*a*), and an enlarged detail of the sensor film including the supporting matrix and luminescence dye in FIG. 2(b). The sensor 1 according to the present invention comprises a magnetic body 11 and a sensor film 12. The magnetic body 11 is susceptible to the external magnetic field. The sensor film 12 comprises a layer with a luminescence dye 121 in a supporting matrix 122, the luminescence dye 121 having a luminescence activity that depends on the concentration of an analyte, e.g. molecular oxygen, carbon dioxide, or glucose, or a physical or chemical parameter, e.g. temperature, or pH.

Luminescence dyes with high quantum yield, large dynamic range, and large Stokes shift can be used, for example, in the sensor film. Known classes of dyes for such purposes are metal-ligand complexes of rhenium (Re), ruthenium (Ru), osmium (Os), or iridium (Ir). To immobilize the dye molecules and achieve selectivity, the dyes are bound to transparent and oxygen permeable supporting matrices, such as e.g. polymers, silica gels, or sol-gels. The supporting matrix should be permeable to the desired analyte such as oxygen and impermeable to most possible interferants such as polar species. Luminophore solubility of the supporting matrix is another important factor for choosing the appropriate supporting matrix.

In the example of a sensor 1 in FIG. 2, the magnetic body 11 is a sphere 3.25 mm in diameter, made of steel, and the sensor film 12 is a thin layer consisting of a supporting matrix 122 made of polystyrene with a distributed luminescence dye 121. In this example, the dye is the N948 Ir(III) dye which is based on an iridium complex, however, this can be any dye known to a person skilled in the art.

The sensor film 12 should not be too thick, since the analyte (e.g. oxygen) must be able to permeate through the sensor film in order to produce the luminescence quench effect throughout the whole layer. The surface of the magnetic body can, for example, be highly reflecting which can result from the manufacturing process itself, i.e., electroplated nickel and/or CoNi, or it can be polished after manufacture, for example, electropolished. This can increase the excitation efficiency and the amount of detectable luminescence signal by increasing the effective layer thickness by a factor of up to two. "Highly reflecting" as understood in the present application means that more than 50%, for example, more than 70% or more than 90%, of at least one spectral band of excitation and/or luminescent emission is reflected.

Figure 3:
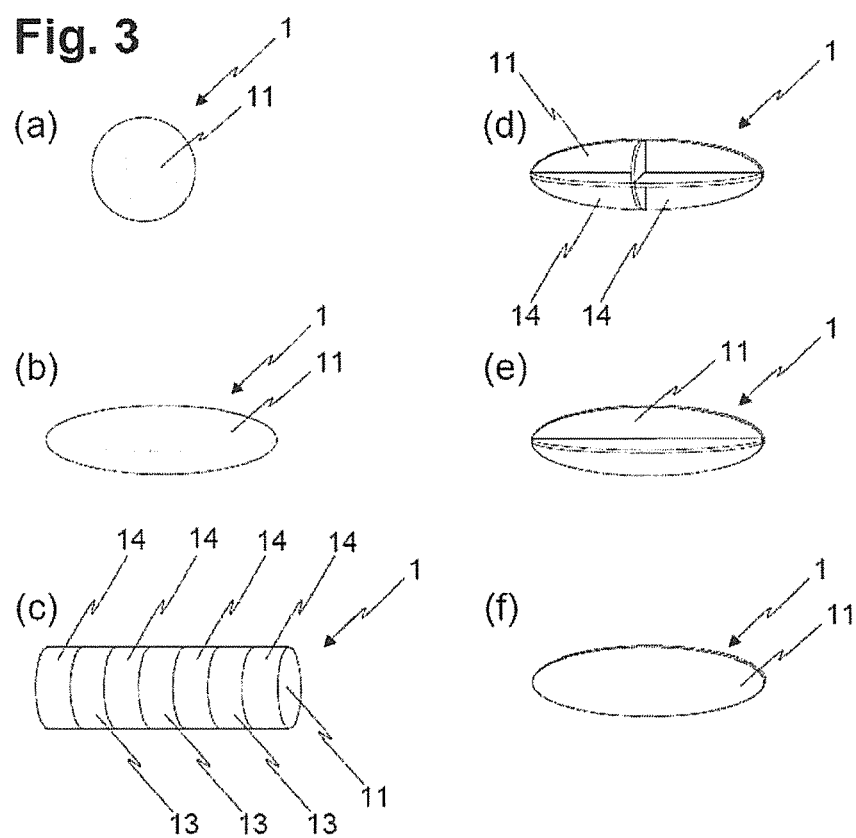
FIG. 3, including

FIG. 3 shows different possible embodiments of sensors 1 according to the present invention. The magnetic body 11 may have any suitable form, such as the form of a sphere, as in FIG. 3(a), a prolate spheroid, as in FIG. 3(b), or a cylinder or a plate, as in FIGS. 3(c) and (f). Depending on their geometry, magnetic bodies can be subject to torques resulting from the applied magnetic field, which may be exploited to orient the magnetic body in the three-dimensional space or even to move the magnetic body.

In addition to objects with simple geometry, such as spheres, spheroids, cylinders, etc., the sensor (as well the underlying magnetic body) also have more complicated shapes, produced for example with the micro electrical mechanical systems fabrication (MEMS) techniques. A soft-magnetic assembled MEMS sensor controlled by applying decoupled magnetic torque and force may be employed in practicing the present invention. Such sensors, as they are shown, for example, in FIGS. 3(d) and (e), comprise two or more parts that are separately produced with MEMS techniques (such as photolithography and electroplating). The sensor prototype is a three-dimensional structure built by microassembly of individual parts. One or more of the assembled parts can be the sensor film. Sensor parts are made with standard or non-standard microfabrication processes such as electroplated nickel, single crystal silicon, polymer and laser cut steel. Different parts can be made using different fabrication processes and then assembled to form a hybrid device.

In an embodiment of the present invention, local concentration gradients of the analyte of interest can be obtained by reading out different locations on the sensor. The sensor 1 given in FIG. 3(c), for example, comprises 4 sensor zones 14 along the cylinder axis of the sensor, separated by spacer areas 13. The different sensor zones 14 can be read out separately.

Two or more luminescence dyes with different emission and/or excitation spectra on different locations of the sensor or at the same location can be used. A readout system that can selectively read out different locations of the sensor can also be used. Concentration gradients can thereby be achieved. As stated above with respect to ratiometric sensors, it is also possible to produce sensors that allow the measurement of more than one emission, one after another, or even at the same time. In this way, measurement of more than one parameter of interest can be achieved.

EXAMPLE

Sensor Film

An embodied luminescence dye for a sensor according to the present invention sensitive to molecular oxygen is an iridium complex dye such as the N948 Ir(III) dye [Ir(2-phenylpyridine)2(4,4'-bis(2-(4-N,N-methylhexylaminophenyl)ethy)-2-2'bipyridine)Cl] whose manufacture and use is described in "Engineering of Efficient Phosphorescent Iridium Cationic Complex for Developing Oxygen-Sensitive Polymeric and Nanostructured Films", Analyst 132 (2007), pages 929-936. The main advantages of an iridium complex dye such as the N948 Ir(III) dye, compared to other metal complex dyes, is its high luminescence quantum yield, high photo-stability, long lifetime, strong absorption band in the visible light region, and larger Stokes shift. The N948 Ir(III) dye has, for example, a peak excitation wavelength at about 494 nm, a peak emission wavelength above 650 nm, and a luminescence quantum yield of above 0.5 in polystyrene. An excitation bandwidth in the visible region can be used, for example, in order to avoid damages to the eye with strong UV excitation light.

Examples of compositions that may additionally be used in the sensor film of the present invention are complexes of iridium or ruthenium. Suitable iridium complexes include $Ir(ppy)_3$, where ppy is 2-phenylpyridine anion, which iridium complex can be obtained from H. W. Sands Corp., Jupiter, Fla., USA. A suitable ruthenium complex includes $Ru(dpp)_3^{2+}$, where dpp is 4,7-diphenyl-1,10-phenanthroline, which ruthenium complex can be obtained from Sigma Aldrich.

Polystyrene is chosen as the supporting matrix in the sensor film because of its high oxygen permeability and biocompatible nature. For sensor film preparation, 3 mg of the N948 Ir(III) dye and 197 mg of polystyrene were dissolved in 2 ml of chloroform by stirring. The probe bodies were then dip-coated with this solution and stored for 2 hours to allow the solvent to evaporate.

EXAMPLE

Detection System

A blue LED was used as the excitation source for the oxygen sensor. A function generator drove the LED circuit with a sinusoidal signal at 1000 Hz. This frequency was chosen to maximize the modulated output signal. A short pass optical filter (cutoff=500 nm, FES0500, Thorlabs GmbH) served to limit the spectrum of excitation to short wavelengths/higher frequencies. A person skilled in the art will know of many alternative excitation sources in addition to a LED including, for example, a laser source or any other suitable light source such as a xenon lamp or laser diode.

Figure 4:
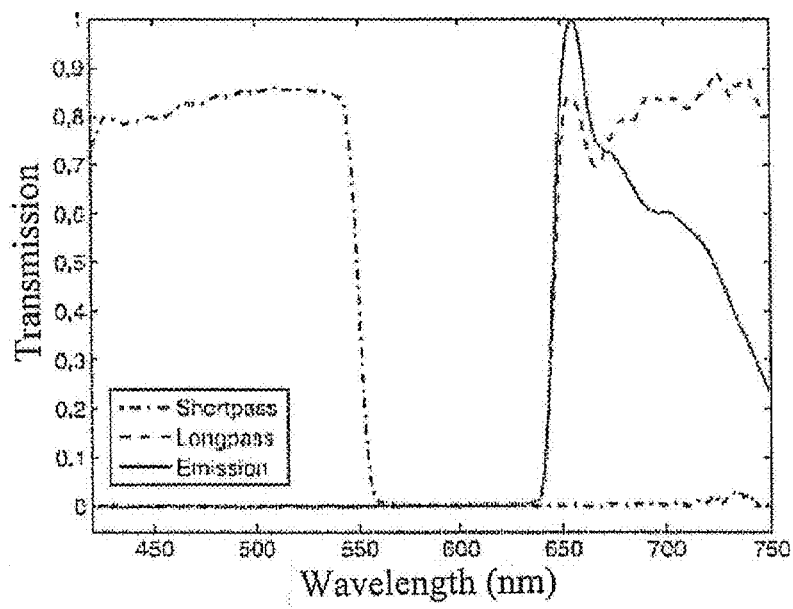
FIG. 4 shows experimentally obtained transmission characteristics of a long pass and low pass filter, and the emission spectrum of a sensor film including the luminescence dye Ir(2-phenylpyridine)2(4,4'-bis(2-(4-N,N-methylhexylaminophenyl)ethy)-2-2'bipyridine)Cl (hereafter "the N948 Ir(III) dye") in a polystyrene matrix.

A long pass optical filter (cutoff=550 nm, FEL0550, Thorlabs GmbH) and a photodiode (PD) served to detect the luminescence, which occurs at longer wavelengths/lower frequencies. The transmission characteristics of the filters and the emission spectrum of the N948 Ir(III) dye were obtained using a spectrometer (AvaSpec-2048, Avantes Inc.), as shown in FIG. 4. A commercial large area amplified Si photo detector in an aluminum housing (PDA100A-EC, Thorlabs GmbH) was used to obtain high photo sensitivity and low noise. A person skilled in the art will know of many alternative detectors in addition to a Si photo detector including, for example, a photomultiplier tubes, CCD detectors.

Using a data acquisition card (NI PCI-6259, National Instruments Corp.), the amplified signal was acquired by a computer, as is the input modulating signal which was used as a reference. The signals were digitally band pass filtered to eliminate the noise at other frequencies, as well as the DC components of the signals. Data acquisition was carried out at a rate of 500 kHz, resulting in a resolution in the time domain of 2 μs. To further increase the time resolution, a sine fitting algorithm using MATLAB software from The MathWorks, Inc. was applied in a numerical computing environment. The curve fitting toolbox of MATLAB was used for this purpose. The fitting algorithm was tested using an electronic delay circuit, resulting in a resolution in the order of 10 ns.

EXAMPLE

Magnetic Body

The sensor film of the present invention was coated on a magnetic body. The magnetic body may be made of a magnetic material such as iron, nickel or cobalt, or their alloys or another material which incorporates magnetic materials such as polymers containing magnetic particles and is as small as possible, for example less than 4 mm in length or less than 0.5 mm or less than 0.25 mm. One suitable alloy combination is, for example, 55% cobalt and 45% nickel. The surface of the magnetic body may be coated with a polymer such as polystyrene or a metal to optimize the sensor and/or to provide for biocompatibility.

Figure 5:
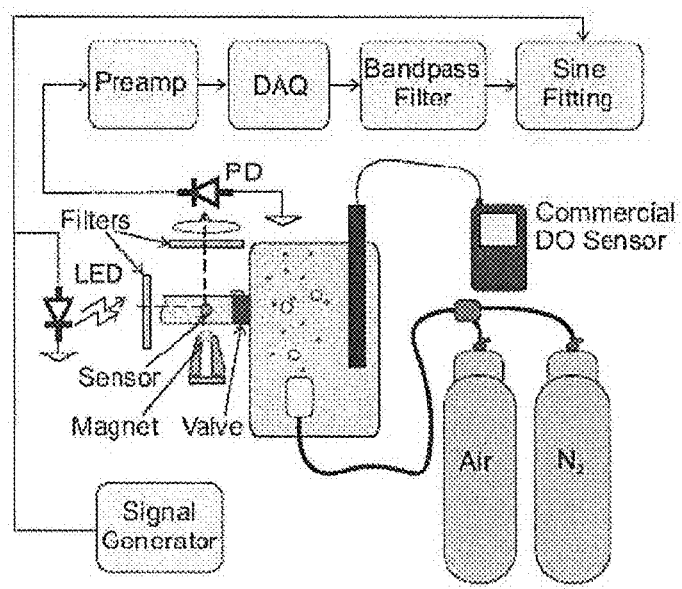
FIG. 5 schematically shows a test setup for measuring the luminescence lifetime of a sensor film at certain oxygen concentrations.

A sensor according to the present invention was produced by coating a magnetic body in the form of a ferromagnetic steel sphere with a diameter of 3.25 mm with the N948 Ir(III) dye/polystyrene layer as described above, acting as the sensor film. To test the sensor, the sensor response was measured as a function of the oxygen concentration in water, with an apparatus according to the present invention. The test setup used is depicted in FIG. 5. The detection system is identical to the one described above. The sensor was immobilized with a constant magnet field gradient. The oxygen concentration was changed by bubbling a mixture of nitrogen and air (oxygen and nitrogen) through water. The oxygen concentration of the calibration solution was determined with a commercial electrochemical oxygen sensor (Oxi340i, WTW GmbH). The lowest and highest oxygen concentration levels tested were 0.25 ppm and 8.27 ppm, respectively. Three measurement cycles were made, going from the lowest concentration level to the highest, and back to the lowest again. Seventeen measurements were taken at different oxygen concentration levels. No ambient light was present.

The experimental setup used to characterize the oxygen sensitivity of the sensor is shown in FIG. 5. The experimental setup comprises two plexiglass containers, one as a source and the other as a sink for deionized water, a pipe connecting these two where the measurements take place, and a valve which provides a sample-and-hold configuration. Plexiglass was chosen as the material because of its transparency in the UV spectrum, which makes it superior to glass for this application. Plexiglass also has a very low gas permeability which makes it effectively an impermeable barrier and keeps the gas concentration as anticipated throughout the experiment. The excitation and readout components described above were placed at different sides of the pipe. Optical filters were used to separate the emission signal from the excitation signal. A signal generator and an excitation circuit were used to generate the excitation signal for the blue LED. A preamplifier (Preamp) was used to amplify the photodiode (PD) signal and a data acquisition card (DAQ) was used to read this signal with a computer. The signal was then bandpass filtered to filter out electronic, background noise and the sine fitting algorithm was used to improve readout sensitivity.

Figure 6:
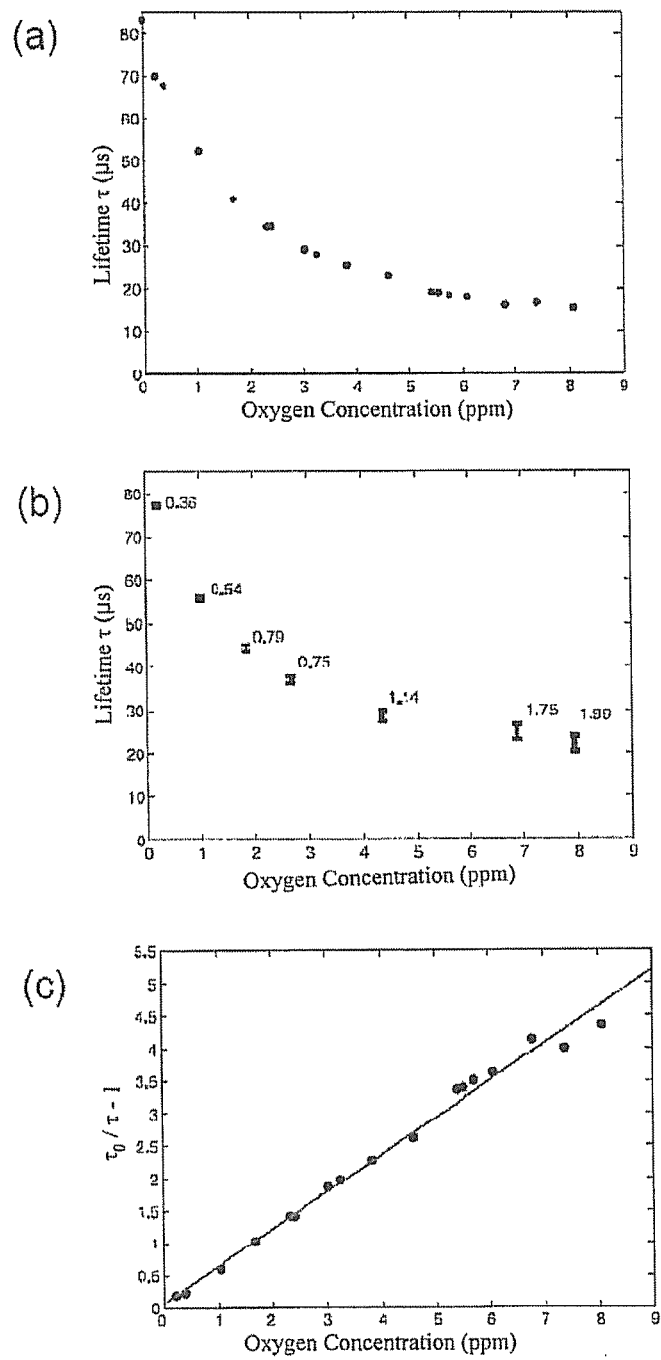
FIG. 6 shows: (a) the measured lifetime of a sensor film including the luminescence of the N948 Ir(III) dye in a polystyrene matrix as a function of the oxygen concentration; (b) the measured luminescence lifetime of the sensor film with standard deviation error bars for ten consecutive measurements; and (c) the luminescence lifetimes of the sensor film in a Stern-Volmer plot.

Deionized water was used to obtain dissolved oxygen measurements The sensor was immersed in the pipe for the measurements and its location was maintained with a permanent magnet. The distances between the components and the sensor were chosen considering the geometry of the eye. The average distance between the cornea and the retina of the human eye is 22.2 mm. Therefore, the distance between the setup components and the sensor was kept larger than 22.2 mm throughout the experiments. One of the containers was filled with water and a range of oxygen concentrations was achieved by bubbling air or nitrogen gas inside said container. Nitrogen replaced oxygen molecules in the solution while air provided oxygen. Consequently, by applying nitrogen, the oxygen concentration could be reduced, and by applying air it could be increased tip to air saturation level at a given pressure and temperature condition. A commercial electrochemical dissolved oxygen sensor (DO) (Oxi340i, WTW GmbH) was used as a reference, which was calibrated at the start of each experiment using its calibration vessel. While bubbling gases into the container, the oxygen concentration was monitored using said sensor. When the desired concentration was reached, the valve of the pipe connecting the two containers was opened to fill the pipe with this solution at known oxygen concentration and then closed again. This made a simple sample-and-hold configuration for the measurement. At the time scales of the experiment, the effect of diffusion on the oxygen concentration inside the pipe was negligible. The lowest and highest oxygen concentration levels achieved were 0.25 ppm and 8.27 ppm, respectively. Three cycles were made going from the lowest concentration level to the highest and back to the lowest again. Seventeen measurements were taken at different oxygen concentration levels without the presence of ambient light. FIGS. 6(a) and (c) shows said measurements as a Stern-Volmer plot as a function of oxygen concentration.

The magnetic body was dip-coated with a polystyrene film-containing iridium complex dye, and good uniformity was achieved across the magnetic body. If needed, an additional layer of pure polystyrene can be added to isolate the sensor film.

FIG. 6(a) shows the lifetime of emission as a function of oxygen concentration. The inherent non-linear dependence of the quenching process on the oxygen concentration, as predicted by the Stern-Volmer equation, is shown in this Figure. FIG. 6(c) shows the measured lifetimes as a Stern-Volmer plot ($\tau_0/\tau-1$ vs. $[O_2]$) for the same data. As seen in this Figure, a linear model proved to be an excellent predictor ($R^2=0.989$) for oxygen concentrations obtained with the commercial sensor. The obtained Stern-Volmer constant was $K=0.567$ ppm$^{-1}$.

FIG. 6(b) shows the lifetime of emission of another sensor of the same type, as a function of oxygen concentration, with the individual numbers listed representing the standard deviation of the lifetime, for ten consecutive measurements. The standard deviation is smaller for low oxygen concentrations, due to the intensity decrease caused by the quenching at higher oxygen concentrations.

The present invention is not to be limited in scope by the specific embodiments described herein. Indeed, various modifications of the present invention, in addition to those described herein, will be apparent to those skilled the art from the foregoing description and accompanying drawings. Thus, such modifications are intended to fall within the scope of the appended claims. Additionally, various references are cited throughout the specification, the disclosures of which are each incorporated herein by reference in their entirety.

List of Reference Numbers
- 1 sensor
- 11 magnetic body
- 12 sensor film
- 121 luminescence dye molecule
- 122 supporting matrix
- 13 spacer area
- 14 sensor zone
- 2 apparatus
- 21 excitation light source
- 211 excitation light beam
- 22 detection device
- 221 light signal
- 24 detection system
- 25 actuation system
- 3 eye
- 31 retina
- 32 vitreous humor
- 33 lens
- 34 aqueous humor
- 35 cornea
- 36 iris
- 37 sclera
- 38 pupil
- B magnetic field
- F magnetic force acting on the sensor

What is claimed is:

1. A sensor for intraocular measurements moveable within at least one of a vitreous humor of an eye, an aqueous humor of an eye and an intraocular replacement medium, the sensor comprising:
   a magnetic body susceptible to magnetic fields; and
   at least one sensor film including a supporting matrix and at least one of a luminescence dye, a fluorescence dye and a phosphorescence dye.

2. The sensor as recited in claim 1, wherein the magnetic body includes at least one of a ferromagnetic material, a ferrimagnetic material, a paramagnetic material and a compound with magnetic properties.

3. The sensor as recited in claim 2, wherein the magnetic body includes the compound with magnetic properties which includes at least one of magnetic particles, nanoparticles and super paramagnetic nanoparticles.

4. The sensor as recited in claim 2, wherein the magnetic body is shaped as a sphere, an oblate spheroid, a prolate spheroid, a plane or a cylinder.

5. The sensor as recited in claim 2, wherein the at least one ferromagnetic material, ferrimagnetic material, paramagnetic material and a compound with magnetic properties is selected from at least one of alloys of iron, nickel and cobalt.

6. The sensor as recited in claim 1, wherein the at least one luminescence dye, fluorescence dye and phosphorescence dye has a luminescence effect susceptible to at least one of a physical parameter, a chemical parameter and the concentration of a chemical analyte.

7. The sensor as recited in claim 1, wherein the supporting matrix includes at least one of a polymer, silica gels and sol-gels.

8. The sensor as recited in claim 7, wherein the polymer is polystyrene.

9. The sensor as recited in claim 1, wherein the at least one luminescence dye, fluorescence dye and phosphorescence dye is at least one of an iridium complex and a ruthenium complex.

10. The sensor as recited in claim 1, wherein the sensor film is disposed on a highly reflecting surface of the magnetic body.

11. The sensor as recited in claim 1, wherein a surface of the magnetic body is coated with at least one of a metal, metal alloy and a polymer.

12. The sensor as recited in claim 11, wherein the at least one metal, metal alloy and polymer is at least one of gold, titanium, polystyrene and polypyrrole.

13. A sensor for at least one in-vivo measurement moveable within at least one of a human or an animal body, the sensor comprising:
   a magnetic body susceptible to magnetic fields; and
   at least one sensor film having a luminescence activity that depends on at least one of a physical parameter, a chemical parameter and the concentration of a chemical analyte.

14. The sensor according to claim 13, wherein the luminescence activity of the at least one sensor film depends on at least one of a molecular oxygen concentration, a carbon dioxide concentration, a glucose concentration, temperature and pH.

* * * * *